(12) United States Patent
Djokic

(10) Patent No.: US 8,399,028 B2
(45) Date of Patent: Mar. 19, 2013

(54) ANTIMICROBIAL SILVER SOLUTIONS

(75) Inventor: Stojan Djokic, Edmonton (CA)

(73) Assignee: Exciton Technologies Inc., Edmonton (CA)

( * ) Notice: Subject to any disclaimer, the term of this patent is extended or adjusted under 35 U.S.C. 154(b) by 955 days.

(21) Appl. No.: 12/191,477

(22) Filed: Aug. 14, 2008

(65) Prior Publication Data

US 2010/0040699 A1 Feb. 18, 2010

(51) Int. Cl.
*A01N 59/16* (2006.01)
*A61K 33/38* (2006.01)

(52) U.S. Cl. .................................................. 424/618

(58) Field of Classification Search .................. None
See application file for complete search history.

(56) References Cited

U.S. PATENT DOCUMENTS

| | | | | |
|---|---|---|---|---|
| 2,345,134 | A | * | 3/1944 | Lindsay et al. ............... 423/265 |
| 3,702,298 | A | | 11/1972 | Zsoldos et al. |
| 3,826,639 | A | * | 7/1974 | Pommer et al. ............... 504/115 |
| 4,291,125 | A | | 9/1981 | Greatbatch |
| 4,385,632 | A | | 5/1983 | Odelhog |
| 4,608,183 | A | | 8/1986 | Rossmoore |
| 4,666,616 | A | | 5/1987 | Rossmoore |
| 4,780,216 | A | | 10/1988 | Wojtowicz |
| 4,915,955 | A | | 4/1990 | Gomori |
| 5,017,295 | A | | 5/1991 | Antelman |
| 5,073,382 | A | | 12/1991 | Antelman |
| 5,078,902 | A | | 1/1992 | Antelman |
| 5,089,275 | A | | 2/1992 | Antelman |
| 5,332,511 | A | | 7/1994 | Gay et al. |
| 5,336,508 | A | | 8/1994 | Marty |
| 5,985,308 | A | | 11/1999 | Burrell et al. |
| 6,197,814 | B1 | | 3/2001 | Arata |
| 6,238,686 | B1 | | 5/2001 | Burrell et al. |
| 6,583,176 | B2 | | 6/2003 | Arata |
| 6,660,289 | B1 | | 12/2003 | Wilmotte et al. |
| 6,686,324 | B2 | | 2/2004 | Ramirez et al. |
| 6,838,095 | B2 | | 1/2005 | Newman et al. |
| 6,890,953 | B2 | | 5/2005 | Arata |
| 6,939,566 | B2 | | 9/2005 | Batarseh et al. |

(Continued)

FOREIGN PATENT DOCUMENTS

GB 2236115 A * 3/1991
WO WO 00/27390 A1 * 5/2000

OTHER PUBLICATIONS

Bailar, J C., "The Oxidation States of Silver" J. Chem. Educ., 1944, vol. 21, No. 11, p. 523.*

(Continued)

*Primary Examiner* — James H Alstrum Acevedo
*Assistant Examiner* — Daniel L Branson
(74) *Attorney, Agent, or Firm* — Rodman & Rodman; Terrence N. Kuharchuk

(57) ABSTRACT

A method for preparing a concentrated solution containing water, citrate ions and silver ions, including providing an amount of trisilver citrate, providing an amount of citric acid, wherein the amount of the citric acid is at least 19 times the amount of the trisilver citrate by weight, and mixing the trisilver citrate and the citric acid in an amount of water to produce the concentrated solution, wherein the amount of water is selected so that the concentrated solution has a citrate ion concentration which is at least 300 grams per liter. A concentrated solution containing water, citrate ions and silver ions, wherein the concentrated solution has a silver ion concentration which is at least 10 grams per liter. A diluted solution prepared by adding water to a concentrated solution containing water, citrate ions and silver ions.

27 Claims, 6 Drawing Sheets

U.S. PATENT DOCUMENTS

| | | | |
|---|---|---|---|
| 7,261,905 B2 | 8/2007 | Arata et al. | |
| 2002/0150628 A1* | 10/2002 | Newman et al. | 424/618 |
| 2003/0147970 A1* | 8/2003 | Newman et al. | 424/618 |
| 2003/0198689 A1* | 10/2003 | Arata | 424/618 |
| 2005/0118281 A1* | 6/2005 | Newman et al. | 424/618 |
| 2006/0051430 A1* | 3/2006 | Arata et al. | 424/618 |
| 2006/0100273 A1 | 5/2006 | Arata | |
| 2007/0185350 A1* | 8/2007 | Arata | 562/584 |

OTHER PUBLICATIONS

Djokic, S., "Synthesis and Antimicrobial Activity of Silver Citrate Complexes" Bioinorganic Chemistry and Applications, 2008, pp. 1-7.*

Persson et al., "Coordination chemistry of the solvated silver(I) ion in the oxygen donor solvents water, dimethyl sulfoxide, and N,N'-Dimethylpropyleneurea" Inorg. Chem. 2006, vol. 45, pp. 7428-7434.*

Silver Citrate Hydrate, www.sigmaaldrich.com/catalog/product/ALDRICH/361259?lang=en&region=US# accessed on Jun. 12, 2012.*

Khlobystov et al., "Supramolecular design of one-dimensional coordination polymers based on silver(I) complexes of aromatic nitrogen-donor ligands" Coordination Chemistry Reviews, 2001, vol. 222, pp. 155-192.*

D. Acel, "Uber die oligodynamische Wirkung der Metalle," Z. Biochem., 112 (1920) pp. 23-26, with English Abstrct, English abstract only.

S.S. Djokic and R.E. Burrell, "Behavior of Silver in Physiological Solutions," Journal of Electrochemical Society, v. 145 (5) pp. 1426-1430.

N.R. Thompson, in "Comprehensive Inorganic Chemistry," V.III D, J.C. Bailer et al, Editors, Pergamon Press, Oxford (1973) pp. 79-80.

D. Acel, "Uber die oligodynamische Wirkung der Metalle," Z. Biochem., 112 (1920) pp. 23-26, with English Abstrct.

S.S. Djokic and R.E. Burrell, "Behavior of Silver in Physiological Solutions," Journal of Electrochemical Society, v. 145 (5) pp. 1426-1430, 1998.

* cited by examiner

ANTIMICROBIAL SILVER SOLUTIONS

TECHNICAL FIELD

Antimicrobial silver solutions and methods for preparing antimicrobial silver solutions.

BACKGROUND OF THE INVENTION

The antimicrobial properties of silver have been utilized for centuries. For example, early Mediterranean cultures recognized that storing water in silver vessels rendered it potable. In the Middle Ages, silver nitrate was used for nervous disorders, epilepsy and for curing syphilis. In 1844, Crede, a German obstetrician, used a silver nitrate solution to eliminate blindness in newborns caused by post-partum infection. A silver nitrate solution was also used by von Behring in 1887 for the treatment of typhoid and anthrax. Other forms of silver such as coatings for the prevention of food spoilage and silver plates and foils for the surgical treatment of wounds and broken bones have also been used throughout the centuries.

It is believed that antimicrobial properties of silver may be provided by silver ions. As a result, efforts have been made in the prior art to produce compositions containing silver ions for use in providing antimicrobial properties. One challenge in producing such compositions is in providing compositions which are relatively "stable", in that the silver ions will remain in ionic form in the compositions before use so that the silver ions are available during use to provide antimicrobial properties. Another challenge in producing such compositions is in providing methods of preparation of the compositions which are relatively economical.

U.S. Pat. No. 6,197,814 (Arata) discloses an aqueous disinfectant comprising an aqueous solution of silver citrate and citric acid produced by a process comprising electrolytically generating silver ions in a solution of citric acid and water, with the silver ions reacting with the citric acid to form electrolytically generated silver citrate having a concentration greater than the concentration of a non-electrolytically generated silver citrate within a similar or same solution of citric acid and water.

U.S. Pat. No. 6,838,095 (Newman et al) discloses a substantially non-colloidal solution made by combining ingredients comprising water, a source of free silver ions, and a substantially non-toxic, substantially thiol-free, substantially water-soluble complexing agent.

There remains a need for relatively economical methods for producing relatively stable aqueous solutions containing relatively high concentrations of silver ions. There also remains a need for relatively stable aqueous solutions containing relatively high concentrations of silver ions which may be used directly or diluted for use as antimicrobial compositions.

SUMMARY OF THE INVENTION

References in this document to operating parameters, to ranges, to lower limits of ranges, and to upper limits of ranges are not intended to provide strict boundaries for the scope of the invention, but should be construed to mean "approximately" or "about" or "substantially", within the scope of the teachings of this document, unless expressly stated otherwise.

Further to the previous paragraph, references in this document to amounts of compounds expressed in "grams", "moles", "% by weight", "ppm" etc. are based upon approximate molar weights of the compounds described. For example, in this document the molar weight of citric acid is considered to be about 192 grams per mole, the molar weight of the citrate ion is considered to be about 189 grams per mole, the molar weight of trisilver citrate is considered to be about 513 grams per mole and the molar weight of silver nitrate is considered to be about 170 grams per mole.

Further to the previous two paragraphs, references in this document to conversions between "grams", "moles", % by weight", "ppm" etc. are approximate conversions. For example, 2 moles of citric acid and 2 moles of the citrate ion are both considered to constitute about 400 grams for the purposes of this document.

The present invention is directed generally at methods for producing solutions comprising water, a suitable carboxylic acid and a suitable silver salt of the carboxylic acid. The present invention is also directed generally at solutions comprising water, a suitable carboxylic acid and a suitable silver salt of the carboxylic acid.

The solutions according to the present invention may be concentrated solutions or diluted solutions. A concentrated solution is a solution prepared in accordance with the invention which has a concentrated silver ion concentration which is at least 10 grams per liter. A diluted solution is a solution which is prepared from a concentrated solution and which has a diluted silver ion concentration which is less than the concentrated silver ion concentration.

A particularly suitable carboxylic acid for use in the invention is citric acid and a particularly suitable silver salt for use in the invention is trisilver citrate. Other potentially suitable carboxylic acids include, but are not limited to, glycolic acid, lactic acid, alpha hydroxybutyric acid, mandelic acid, glyceric acid, malic acid, tartaric acid, and meso-tartaric acid.

Trisilver citrate exhibits relatively low solubility in water under normal physico-chemical conditions (i.e., room temperature and atmospheric pressure). According to the Merck Index, the solubility of trisilver citrate in water is about 1 part trisilver citrate in 3500 parts water (i.e., about 285 parts per million (ppm) or about 0.285 grams per liter or about 0.0026 moles per liter).

The invention is based in part upon the discovery that trisilver citrate exhibits relatively higher solubility in an aqueous solution of citric acid, which solubility is proportionate to the concentration of the citric acid (i.e., citrate ions) in the aqueous solution.

The invention is also based in part upon the discovery that a solution comprising water, citrate ions, and trisilver citrate can be relatively stable, depending upon the concentration of the citric acid and the concentration of the silver ions in the aqueous solution. For the purposes of this document, a "stable" solution is a solution in which substantially all of the silver ions initially present in the solution will remain in the solution for an extended period of time.

The solubility of silver ions in an aqueous solution of citric acid and the stability of such a solution is believed to result at least in part from the formation of one or more relatively soluble silver citrate complexes in the solution.

More particularly, the invention is based in part upon the following observed properties which have been found to be generally applicable under normal physico-chemical conditions to solutions comprising water, citric acid (i.e., citrate ions) and silver ions and which are applied in the practice of the invention:

1. the solubility of silver ions in the solution increases in a substantially linear relationship with the concentration of the citric acid as the concentration of the citric acid in the aqueous solution increases from 0 to about 4 moles per liter (i.e., about 800 grams per liter, or about 45% by weight).

2. pursuant to the linear relationship described above, at least about 30 grams (i.e., about 0.16 moles) of citric acid are required to be dissolved in the solution for each gram (i.e., about 0.0093 moles) of silver ions which are dissolved in the solution;

3. pursuant to the linear relationship described above, at least about 19 grams (i.e., about 0.099 moles) of citric acid are required to be dissolved in the solution for each gram (i.e., about 0.0020 moles) of trisilver citrate which is dissolved in the solution;

4. at a citric acid concentration in the solution of about 4 moles per liter (i.e., about 800 grams per liter, or about 45% by weight), a silver ion concentration of about 25 grams per liter (i.e., about 25000 ppm or about 0.23 moles per liter) can be achieved in the solution;

5. at a citric acid concentration in the solution of about 2 moles per liter (i.e., about 400 grams per liter, or about 29% by weight), a silver ion concentration of about 13 grams per liter (i.e., about 13000 ppm or about 0.12 moles per liter) can be achieved in the solution;

6. at a citric acid concentration in the solution of about 1.5 moles per liter (i.e., about 300 grams per liter, or about 23% by weight), a silver ion concentration of about 10 grams per liter (i.e., about 10000 ppm or about 0.093 moles per liter) can be achieved in the solution;

7. a solution having a silver ion concentration less than or equal to about 13 grams per liter (i.e., about 13000 ppm or about 0.12 moles per liter) is relatively stable, in that the silver ion concentration in the solution will remain substantially constant over time;

8. a stabilizing agent may be added to a solution having a silver ion concentration greater than about 13 grams per liter (i.e., about 13000 ppm or about 0.12 moles per liter) in order to enhance the stability of the solution. A suitable stabilizing agent may be comprised of glycerol;

9. a diluted solution having a silver ion concentration less than or equal to about 13 grams per liter (i.e., about 13000 ppm or about 0.12 moles per liter) which is prepared by adding water to a concentrated solution having a silver ion concentration greater than about 13 grams per liter (i.e., about 13000 ppm or about 0.12 moles per liter) is relatively stable, in that the silver ion concentration in the solution will remain substantially constant over time;

The above observed properties are based upon an approximate molar weight for citric acid of about 192 grams per mole, an approximate molar weight for silver of about 108 grams per mole, an approximate molar weight for citrate ions of about 189 grams per mole, and an approximate molar weight for trisilver citrate of about 513 grams per mole.

Having regard to the above observed properties, in one composition aspect the invention may be a concentrated solution comprising water, citrate ions and silver ions, wherein the citrate ions have a concentrated citrate ion concentration in the concentrated solution which is at least 300 grams per liter and wherein the silver ions have a concentrated silver ion concentration in the concentrated solution which is at least 10 grams per liter.

Having regard to the above observed properties, in another composition aspect the invention may be a diluted solution prepared by adding water to a concentrated solution comprising water, citrate ions and silver ions, wherein the silver ions have a concentrated silver ion concentration in the concentrated solution which is greater than 10 grams per liter, wherein the citrate ions have a concentrated citrate ion concentration in the concentrated solution which is at least 30 times the concentrated silver ion concentration by weight, wherein the silver ions have a diluted silver ion concentration in the diluted solution which is less than the concentrated silver ion concentration, and wherein the citrate ions have a diluted citrate ion concentration in the diluted solution which is at least 30 times the diluted silver ion concentration by weight.

Having regard to the above observed properties, in one method aspect the invention may be a method for preparing a concentrated solution comprising water, citrate ions and silver ions, the method comprising:

(a) providing an amount of trisilver citrate;
(b) providing an amount of citric acid, wherein the amount of citric acid is at least 19 times the amount of the trisilver citrate by weight; and
(c) mixing the trisilver citrate and the citric acid in an amount of water to produce the concentrated solution, wherein the amount of the water is selected so that the concentrated solution has a concentrated citrate ion concentration in the concentrated solution which is at least 300 grams per liter.

The method of the invention may be performed at any temperature between about 2 degrees Celsius and about 100 degrees Celsius. A preferred temperature range for the performance of the method is between about 20 degrees Celsius and about 40 degrees Celsius. Increasing the temperature of the performance of the method may be advantageous for increasing the solubility of the citrate ions and the silver ions in the concentrated solution and for increasing the rate at which the method may be performed.

The concentrated citrate ion concentration may be between 300 grams per liter and the maximum citrate ion concentration which may be achieved under the physico-chemical conditions of the solution. At normal physico-chemical conditions, the maximum citrate ion concentration in an aqueous solution of citric acid is believed to be about 1550 grams of citrate ion per liter of water.

As a result, the concentrated citrate ion concentration may be between 300 grams per liter and 1550 grams per liter under normal physico-chemical conditions.

A concentrated citrate ion concentration above about 800 grams per liter may be difficult to achieve and maintain and the solubility of silver ions in solutions containing more than 800 grams per liter of citrate ions may cease to increase in a linear relationship.

As a result, in some embodiments the concentrated citrate ion concentration is between 300 grams per liter and 800 grams per liter under normal physico-chemical conditions.

At a concentrated citrate ion concentration of 800 grams per liter, the concentrated silver ion concentration is about 25 grams per liter. At a concentrated citrate ion concentration of 300 grams per liter, the concentrated silver ion concentration is about 10 grams per liter. At a concentrated citrate ion concentration of 400 grams per liter, the concentrated silver ion concentration is about 13 grams per liter.

As a result, in some embodiments in which the concentrated citrate ion concentration is between 300 grams per liter and 1550 grams per liter, the concentrated silver ion concentration is between 10 grams per liter and 25 grams per liter. In some embodiments in which the concentrated citrate ion concentration is between 300 grams per liter and 800 grams per liter, the concentrated silver ion concentration is between 10 grams per liter and 25 grams per liter. In some embodiments in which the concentrated citrate ion concentration is at least 400 grams per liter, the concentrated silver ion concentration is greater than 13 grams per liter.

Water may be added to the concentrated solution to prepare a diluted solution. The water which is added to the concentrated solution may be purified water, such as water which has been subjected to distillation, deionization, reverse osmosis, filtration or some other purification processes.

In some applications, the water which is added to the concentrated solution may be unpurified water, depending upon the impurities which may be contained in the available unpurified water. If the available unpurified water contains impurities which may significantly interfere with the solubility of the silver ions in the concentrated solution, it is preferred that the water which is added to the concentrated solution to prepare the diluted solution is purified water.

The citrate ions have a diluted citrate ion concentration in the diluted solution and the silver ions have a diluted silver ion concentration in the diluted solution. The diluted silver ion concentration is less than the concentrated silver ion concentration. The diluted citrate ion concentration is at least 30 times the diluted silver ion concentration by weight.

In some embodiments, the diluted silver ion concentration is greater than 13 grams per liter. In some embodiments, the diluted silver ion concentration is less than or equal to 13 grams per liter. In some embodiments, the diluted silver ion concentration is less than or equal to 10 grams per liter.

A plurality of diluted solutions having the same or different diluted silver ion concentrations may be prepared from the concentrated solution. A diluted solution may also be further diluted. The preparation of one or more diluted solutions from the concentrated solution facilitates the production of the concentrated solution with a relatively high silver ion concentration (i.e., at least 10 grams per liter) for use as a starting material in the preparation of diluted solutions having silver ion concentrations suited for particular antimicrobial or biomedical applications.

If the concentrated silver ion concentration is greater than 13 grams per liter, the stability of the concentrated solution may be compromised. In such embodiments, the concentrated solution may be diluted to provide a diluted silver ion concentration which is less than or equal to 13 grams per liter so that the diluted solution is relatively stable.

Alternatively, the stability of a concentrated solution and/or of a diluted solution having a silver ion concentration which is greater than 13 grams per liter may be enhanced by including an amount of a stabilizing agent in the solution.

The stabilizing agent may be comprised of any suitable substance or combination of substances which will assist in maintaining the silver ions in the solution. For example, the stabilizing agent may be comprised of glycerol.

The concentrated solution and/or the diluted solution may consist essentially of the water, the citrate ions, the silver ions, and optionally the stabilizing agent. Alternatively, the concentrated solution may be comprised of the water, the citrate ions, the silver ions, and optionally the stabilizing agent.

In some applications, it is preferred that the concentrated solution and/or the diluted solution consists essentially of the water, the citrate ions, the silver ions, and optionally the stabilizing agent. In such applications, any preparation of the diluted solution is preferably performed by adding purified water to the concentrated solution.

If the concentrated solution and/or the diluted solution contains ions or substances in addition to the water, the citrate ions, the silver ions, and optionally the stabilizing agent, such ions or substances preferably do not significantly affect negatively the solubility of the silver ions in the solution. For example, preferably the concentrated solution and/or the diluted solution does not contain "counter-ions" which compete with the silver ions for interaction with the citrate ions to form the silver citrate complexes in the solution.

Citric acid and trisilver citrate are both solids at normal physico-chemical conditions. As a result, the preparation of the concentrated solution may be performed by dissolving an amount of solid citric acid and an amount of trisilver citrate in an amount of water.

The trisilver citrate may be obtained for use in the invention as a solid which is relatively insoluble in water. Alternatively, the trisilver citrate may be prepared from a source of silver ions and a source of citrate ions in a preliminary process which is carried out prior to or as part of the performance of the method of the invention.

As one non-limiting example, the trisilver citrate may be prepared for use in the invention using a "sodium hydroxide route" in which aqueous silver nitrate is reacted with aqueous sodium hydroxide to produce silver oxide as a precipitate, and in which the silver oxide precipitate is reacted with aqueous citric acid to produce trisilver citrate as a precipitate.

As a second non-limiting example, the trisilver citrate may be prepared for use in the invention using an "ammonium hydroxide route" in which aqueous silver nitrate is reacted with aqueous ammonium hydroxide to produce soluble silver diamino complexes which are then reacted with citric acid to produce trisilver citrate as a precipitate.

As a third non-limiting example, the trisilver citrate may be prepared for use in the invention using a "silver oxide route" in which silver oxide solid is reacted with aqueous citric acid to produce trisilver citrate as a precipitate.

As a fourth non-limiting example, the trisilver citrate may be prepared for use in the invention using a "silver salt-citrate compound route" in which an aqueous silver salt (such as silver nitrate) is reacted with an aqueous citrate compound (such as ammonium citrate or a citrate salt) to produce trisilver citrate as a precipitate.

As a fifth non-limiting example, the trisilver citrate may be prepared for use in the invention using an "electrolytic chemistry route" in which electrolysis is performed using a silver electrode as a source of silver ions in an electrolytic solution of citrate ions in order to produce trisilver citrate in solution or as a precipitate.

The various routes for preparing trisilver citrate may produce one or more substances in addition to trisilver citrate as a product. If the concentrated solution is to consist essentially of the water, the citrate ions, the silver ions, and optionally the stabilizing agent, then the trisilver citrate may be separated from such other substances before being used in the method of the invention. Separating the trisilver citrate from such other substances may be performed by filtering, by washing and/or by using other suitable separation techniques.

The concentrated solutions and diluted solutions prepared in accordance with the invention may be diluted with water to provide any desired silver ion concentration. Concentrated solutions and diluted solutions prepared in accordance with the invention and having a silver ion concentration which is less than or equal to 13 grams per liter are relatively stable. Concentrated solutions and diluted solutions having a silver ion concentration greater than 13 grams per liter may be rendered more stable by being diluted with water to provide a silver ion concentration which is less than or equal to 13 grams per liter.

The concentrated solutions and diluted solutions prepared in accordance with the invention may be used in many different applications where the antimicrobial properties of silver ions may be useful. By way of non-limiting examples, concentrated solutions and/or diluted solutions prepared in accordance with the invention may be used (depending upon the silver ion concentration) as disinfectants or cleaning agents in swimming pools, hot tubs, hospitals, buildings, aircraft, buses, automobiles, for disinfecting protective masks, surgical instruments, wound dressings, countertops, surgical beds, for preventing biofilm formation, for agricultural applications, and for veterinary medicine applications.

In addition to providing the benefits of the antimicrobial properties of silver ions, the concentrated solutions and diluted solutions prepared in accordance with the invention may provide also benefits resulting from the anti-oxidative properties of citrate ions. The anti-oxidative properties of citrate ions may be useful for treating many different medical conditions. By way of non-limiting examples, the anti-oxidative properties of citrate ions may be useful for the treatment of cancer, conjunctivitis, acne, flu, eye infections, burns and urinary tract infections.

As a result, the concentrated solutions and the diluted solutions prepared in accordance with the invention may provide in a single composition or product the combined effects of the antimicrobial properties of silver ions and the anti-oxidative properties of citrate ions.

The concentrated solutions and the diluted solutions prepared in accordance with the invention may be used in any suitable manner. By way of non-limiting examples, the concentrated solutions and the diluted solutions may be sprayed onto surfaces or objects, added to other liquids, and/or objects may be soaked in the concentrated solutions and the diluted solutions.

BRIEF DESCRIPTION OF DRAWINGS

Embodiments of the invention will now be described with reference to the accompanying drawings, in which.

DETAILED DESCRIPTION

Figure 1:
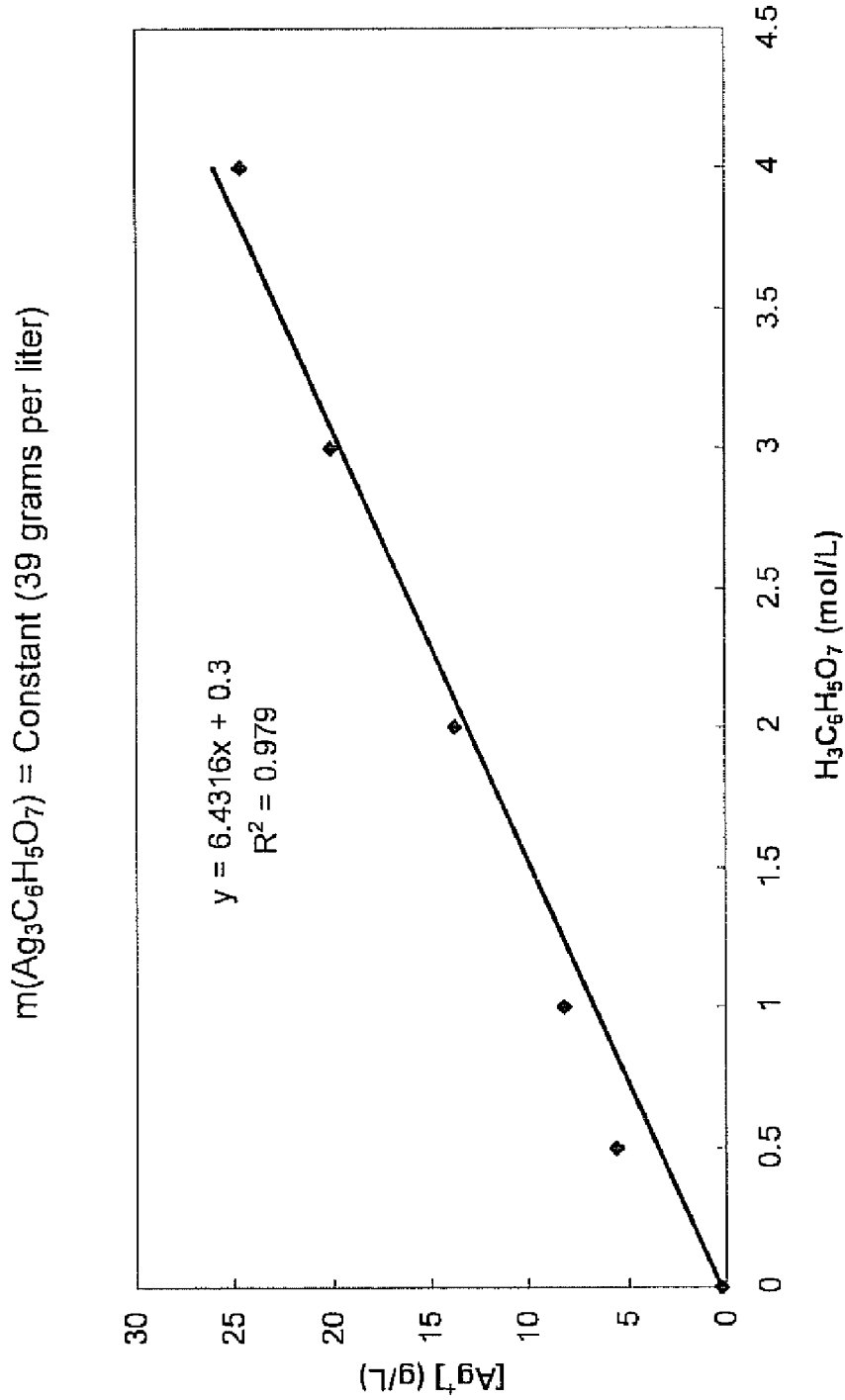
FIG. 1 is a graph depicting a "best fit" of silver ion concentration (in grams per liter) in an aqueous solution as a function of citric acid concentration (in moles per liter) in the aqueous solution, in which a substantially linear relationship is observed for a citric acid concentration between 0 moles per liter and about 4 moles per liter, in which about 39 grams per liter of solid trisilver citrate have been provided in the aqueous solution, and in which the maximum citric acid concentration is about 4 moles per liter.

Trisilver citrate ($Ag_3C_6H_5O_7$) is a white solid compound which exhibits relatively low solubility in water ($H_2O$) under normal physico-chemical conditions (i.e., room temperature and atmospheric pressure).

The present invention is directed at methods for the preparation of silver citrate complexes which are soluble in water, at concentrated solutions containing relatively high concentrations of such silver citrate complexes, and at diluted solutions prepared from such concentrated solutions.

The maximum silver ion concentration that can be achieved in solution by the present invention is estimated at about 25 grams of silver ions ($Ag(I)$) per liter (i.e., about 25,000 ppm or about 0.23 moles per liter). Concentrated solutions of silver ions prepared in accordance with the invention can be diluted (without causing the precipitation of silver salt(s)) to provide diluted solutions which can be used for antimicrobial and/or disinfectant applications throughout a wide range of silver ion concentrations, including low silver ion concentrations of between 5 ppm and 60 ppm, depending on the targeted application.

Although trisilver citrate is not soluble to a significant extent in water, it can be dissolved in aqueous citric acid solutions under appropriate conditions as described in this document.

Citric acid ($H_3C_6H_5O_7$) is a solid which is relatively soluble in water. If citric acid is added to a slurry containing solid particles of trisilver citrate, the dissolution of the trisilver citrate in the resulting aqueous solution can theoretically be represented by the following Equations:

$$Ag_3C_6H_5O_7\downarrow + 2H_3C_6H_5O_7 \rightarrow 3AgH_2C_6H_5O_7 \qquad (1)$$

and

$$2Ag_3C_6H_5O_7\downarrow + H_3C_6H_5O_7 \rightarrow 3Ag_2HC_6H_5O_7 \qquad (2)$$

if the compounds $AgH_2C_6H_5O_7$ and $Ag_2HC_6H_5O_7$ are soluble in water.

Based upon the stoichiometry of Equations (1) and (2) and upon an assumption that the compounds $AgH_2C_6H_5O_7$ and $Ag_2HC_6H_5O_7$ are soluble in water, it can easily be calculated that the required amounts of solid citric acid to achieve a dissolution of 100 grams (about 0.195 moles) of trisilver citrate are, respectively, for Equation (1) about 74.89 grams (about 0.39 moles), and for Equation (2) about 18.72 g (about 0.098 moles).

However, experimental data has proven to be inconsistent with the calculated amounts suggested by Equations (1) and (2). Experimentally, it has been found that significantly larger amounts of citric acid than the amounts suggested by Equations (1) and (2) are required for the dissolution of trisilver citrate.

It has been observed experimentally that with heating it is possible to achieve citric acid concentrations in aqueous solutions of about 1550 grams of citric acid per liter of water (i.e., about 8 moles per liter, or about 61% by weight). It has also been observed experimentally that silver ion concentrations of up to about 25 grams of silver ions per liter of water (i.e., about 25000 ppm or about 0.23 moles per liter) can be achieved in concentrated solutions having a citric acid concentration or citrate ion concentration of at least about 800 grams per liter (i.e., about 4 moles per liter, or about 45% by weight).

Based upon these experimental observations, it seems that the dissolution of trisilver citrate in an aqueous citric acid solution cannot be accurately described by Equations (1) and (2).

Instead, it is believed that the dissolution of trisilver citrate in an aqueous citric acid solution can be described by the following Equations:

$$Ag_3C_6H_5O_7\downarrow + nH_3C_6H_5O_7 \rightarrow [Ag_3C_6H_5O_7(C_6H_5O_7)_n]^{3n-} + 3nH^+ \quad (3)$$

or $$Ag_3C_6H_5O_7\downarrow + nH_3C_6H_5O_7 \rightarrow [Ag_3(C_6H_5O_7)_{n+1}]^{3n-} + 3nH^+ \quad (4)$$

Concentrated solutions and diluted solutions comprising water, citrate ions and silver ions prepared in accordance with the invention (and which are believed to contain silver citrate complexes having the general formula $[Ag_3(C_6H_5O_7)_{n+1}]^{3n-}$) have been found to be relatively soluble and relatively stable in water under certain conditions as described in this document.

To avoid the use of electrochemical equipment, and thereby achieve savings in time and energy, the concentrated solutions of the invention can be produced using many different routes, a number of which are described in this document as non-limiting examples. The production of concentrated solutions according to the invention is not limited to the routes described herein. Other possible routes for production of the concentrated solutions will be apparent to persons skilled in the art by using and modifying the techniques described herein.

It is known that silver salts of carboxylic acids or, more specifically hydroxy acids, may be prepared as white precipitates upon mixing aqueous solutions of silver nitrate and a soluble salt of the carboxylic acid of interest. Consequently, examples of possible chemical routes for the production of concentrated solutions according to the invention include the following.

A. Sodium Hydroxide (NaOH) Route

Starting from a water soluble salt, such as for example silver nitrate ($AgNO_3$), an addition of the required amount of sodium hydroxide (NaOH) would lead to the precipitation of silver oxide ($Ag_2O$), according to the following Equation:

$$2AgNO_3 + NaOH \rightarrow Ag_2O\downarrow + 2NaNO_3 + H_2O \quad (5)$$

If the silver oxide precipitate is properly separated and properly washed, then the addition of a stoichiometrically proper amount of citric acid solution will result in a complete precipitation of silver as trisilver citrate. To avoid silver loses in the process, the conditions are selected such that the yield of the precipitated trisilver citrate is always between about 97% and about 100%. The formation of trisilver citrate upon an addition of citric acid solution to the silver oxide precipitate is described by the Equation:

$$3Ag_2O\downarrow + 2H_3C_6H_5O_7 \rightarrow 2Ag_3C_6H_5O_7\downarrow + 3H_2O \quad (6)$$

As Equation (6) shows, under proper conditions only trisilver citrate and water will be produced. No other constituents will be formed, and a product of high quality and purity will be achieved if the starting materials are free of contaminants.

If an appropriate amount of citric acid is added to the above slurry containing trisilver citrate, then the formation of a concentrated solution containing silver citrate complexes having the general formula $[Ag_3(C_6H_5O_7)_{n+1}]^{3n-}$ may occur as described by Equation (4) above.

Similar processes for the production of concentrated solutions according to the invention are possible if instead of NaOH, other alkali or earth-alkali hydroxides are used in the process.

B. Ammonium Hydroxide ($NH_4OH$) Route

This route can be attractive because silver oxide is soluble in ammonium hydroxide and separation of trisilver citrate from other substances can potentially be avoided for some applications in which the presence of such other substances can be tolerated.

In this route, if ammonium hydroxide ($NH_4OH$) is added to an aqueous solution of silver nitrate, a formation of soluble silver diamino complexes may occur as described by the following Equations:

$$2AgNO_3 + 2NH_4OH \rightarrow Ag_2O\downarrow + 2NH_4NO_3 + H_2O \quad (7)$$

$$Ag_2O\downarrow + 4NH_4OH \rightarrow 2[Ag(NH_3)_2]OH + 3H_2O \quad (8)$$

or, $$AgNO_3 + 3NH_4OH \rightarrow [Ag(NH_3)_2]OH + NH_4NO_3 + 2H_2O \quad (9)$$

To avoid an unnecessary accumulation of ammonium ($NH_4^+$) ions in the system it is recommended that only a stoichiometrically proper amount of ammonium hydroxide be added. This proper amount is determined by the last drop of ammonium hydroxide that leads to the dissolution of the silver oxide which is formed as an intermediate product in the process. If the system contains an excessive amount of ammonium ions, it will be necessary to add additional citric acid in order to neutralize the base and to allow a proper precipitation of the trisilver citrate.

An addition of citric acid to the silver diamino complex solution leads to the precipitation of trisilver citrate as shown by the following Reaction:

$$3[Ag(NH_3)_2]OH + 2H_3C_6H_5O_7 \rightarrow Ag_3C_6H_5O_7\downarrow + (NH_4)_3C_6H_5O_7 + NH_4NO_3 \quad (10)$$

If the presence of ammonium ions in the system can be tolerated, then separation of the trisilver citrate from the solution can be avoided. However, ammonium ions represent a potential "counter-ion" which could compete with silver ions and interfere with the formation of silver citrate complexes, thereby reducing the effectiveness of the method of the invention and the resulting concentrated solution.

As a result, a separation step may be desirable in order to separate the trisilver citrate from the solution and thereby obtain pure trisilver citrate.

Once the trisilver citrate precipitate is formed and optionally separated from the ammonium ions, a further addition of citric acid will produce a concentrated solution containing silver citrate complexes according to the invention.

The amount of citric acid which is required to produce a concentrated solution having a desired silver ion concentration is dependent upon the amount of trisilver citrate and therefore the amount of silver ions and upon the initial amount of silver nitrate which is used to prepare the trisilver citrate.

C. Silver Oxide ($Ag_2O$) Route

Based on the description of Routes A and B above, it is obvious that trisilver citrate can be produced by a route using silver oxide as a source of silver ions. In this route, if a stoichiometrically proper amount of citric acid is added to a slurry containing solid silver oxide, trisilver citrate precipitate will be produced according to the following Equation:

$$3Ag_2O + 2H_3C_6H_5O_7 \rightarrow 2Ag_3C_6H_5O_7\downarrow + 3H_2O \tag{11}$$

An appropriate amount of citric acid may then be mixed with the trisilver citrate in an aqueous solution in order to produce a concentrated solution having a desired silver ion concentration in the manner as described for Routes A and B.

D. Silver Salt-Citrate Compound Route

For this route any water soluble citrate can be used in order to produce the trisilver citrate. One example, using sodium citrate ($Na_3C_6H_5O_7$) is as follows.

If a stoichiometrically proper amount of solid or dissolved sodium citrate is added to an aqueous solution of silver nitrate, precipitation of trisilver citrate will occur according to the following Equation:

$$3AgNO_3 + Na_3C_6H_5O_7 \rightarrow Ag_3C_6H_5O_7\downarrow + 3NaNO_3 \tag{12}$$

After separation of the trisilver citrate precipitate from the sodium nitrate solution, a concentrated solution having a desired silver ion concentration can be produced as described for Routes A and B by mixing the trisilver citrate with an aqueous solution containing an appropriate amount of citric acid.

If the starting compound which is used as a source of citrate ions is ammonium citrate (($NH_4)_3C_6H_5O_7$), the precipitation of trisilver citrate will occur according to the following Equation:

$$3AgNO_3 + (NH_4)_3C_6H_5O_7 \rightarrow Ag_3C_6H_5O_7\downarrow + 3NH_4NO_3 \tag{13}$$

In general terms, the precipitation of trisilver citrate, depending on the source or citrate ions and silver ions, can be described by the following general Equation:

$$Me(I)_3C_6H_5O_7 + 3AgY \rightarrow Ag_3C_6H_5O_7\downarrow + 3MeY \tag{14}$$

where AgY is any water soluble silver salt and Me(I) can be any mono-valent metal or $NH_4^+$.

When the source of the citrate ions is a citrate salt of a two-valent metal, Me(II), the precipitation of trisilver citrate can be described by the following Equation:

$$Me(II)_3(C_6H_5O_7)_2 + 6AgY \rightarrow 2Ag_3C_6H_5O_7\downarrow + 3MeY_2 \tag{15}$$

When the source of the citrate ions is a citrate salt of a three-valent metal, Me(III), the precipitation of trisilver citrate can be described by the following Equation:

$$Me(III)C_6H_5O_7 + 3AgY \rightarrow Ag_3C_6H_5O_7\downarrow + MeY_3 \tag{16}$$

E. Trisilver Citrate Route

The following general method can be used for the production of concentrated solutions containing silver citrate complexes in accordance with the invention.

If available, trisilver citrate can be used directly as a starting material. Alternatively, trisilver citrate which has been produced from sources of silver ions and citrate ions by a route for producing trisilver citrate (including but not limited to Routes A, B, C and D) may be used as the starting material.

In this general method, dissolution of the trisilver citrate in an aqueous solution containing an appropriate amount of citric acid can be carried out in a manner described in Routes A, B, C. and D above, and a concentrated solution containing soluble silver citrate complexes having the general formula $[Ag_3(C_6H_5O_7)_{n+1}]^{3-}$ can be produced.

In summary, Routes A, B, C, D and E represent examples of possible chemical routes for producing concentrated solutions according to the invention. Routes A, B, C and D provide for the production of concentrated solutions according to the invention in which trisilver citrate is not used as a starting material but is produced from a source of silver ions and a source of citrate ions. The produced trisilver citrate is then combined with water and citric acid in order to prepare concentrated solutions according to the invention. Route E is a general route in which trisilver citrate is used as a starting material, wherein the trisilver citrate may be obtained from any source, including a route for producing trisilver citrate from a source of silver ions and a source of citrate ions.

The concentrated solutions according to the invention are comprised of water, citrate ions and silver ions. The concentrated solutions according to the invention may contain other substances as additives or impurities. Preferably, the concentrated solutions according to the invention do not contain material amounts of additives or impurities which interfere with the formation and/or maintenance of silver citrate complexes in the concentrated solutions. As a result, in some embodiments the concentrated solutions consist essentially of water, citrate ions and silver ions such that any other substances which are present in the concentrated solutions do not interfere significantly with the formation and/or maintenance of silver citrate complexes in the concentrated solutions.

Concentrated solutions prepared in accordance with the present invention may be diluted to any silver ion concentration in order to produce diluted solutions for specific antimicrobial applications. Concentrated solutions and diluted solutions prepared in accordance with the invention may be relatively stable depending upon their composition and may be useful within a wide range of antimicrobial and/or disinfectant applications.

The preparation of concentrated solutions and diluted solutions according to the invention requires careful management of the amount of citric acid (i.e., the citric acid concentration or citrate ion concentration) which is present in the solutions, since the solubility of trisilver citrate and the resulting formation of silver citrate complexes is dependent upon the citric acid or citrate ion concentration in the solutions.

The principles guiding the management of the citric acid or citrate ion concentration in concentrated solutions and diluted solutions may be demonstrated with reference to FIGS. 1-6.

FIGS. 1-6 provide results of laboratory experiments conducted for the purpose of establishing the principles and limits relating to the practice of the invention.

FIG. 1 is a graph depicting a "best fit" of silver ion concentration (in grams per liter) in an aqueous solution/slurry containing citric acid and trisilver citrate under normal physico-chemical conditions, as a function of citric acid concentration (in moles per liter), wherein the initial concentration of trisilver citrate in the solution/slurry is 39 grams per liter (i.e., about 24.6 grams per liter of silver).

As can be seen from FIG. 1, an increase in the citric acid concentration leads to an increase in the solubility of silver citrate and thus an increase in the silver ion concentration in the solution.

From FIG. 1, it can be seen that the relationship between citric acid concentration and silver ion concentration is substantially linear for citric acid concentrations between 0 moles per liter and about 4 moles per liter (i.e., about 800 grams per liter or about 45% by weight). The linear relationship may be expressed by the following Equation:

$$y = 6.4316x + 0.3 \tag{17}$$

where: y: is silver ion concentration in grams per liter
x: is citric acid concentration in moles per liter As can be seen, the slope of Equation 17 representing the linear relationship is 6.4316, which means that 6.4316 grams of silver ions are soluble in a liter of water for each mole per liter of citric acid which is present in the solution/slurry.

As a result, a silver ion concentration of about 13 grams per liter (i.e., about 13000 ppm or about 0.12 moles per liter) would appear to be achievable in a solution having a citric acid concentration of about 2 moles per liter (i.e., about 400 grams per liter or about 29% by weight), and a silver ion concentration of about 25 grams per liter (i.e., about 25000 ppm or about 0.23 moles per liter) would appear to be achievable in a solution having a citric acid concentration of about 4 moles per liter (i.e., about 800 grams per liter or about 45% by weight).

Figure 2:
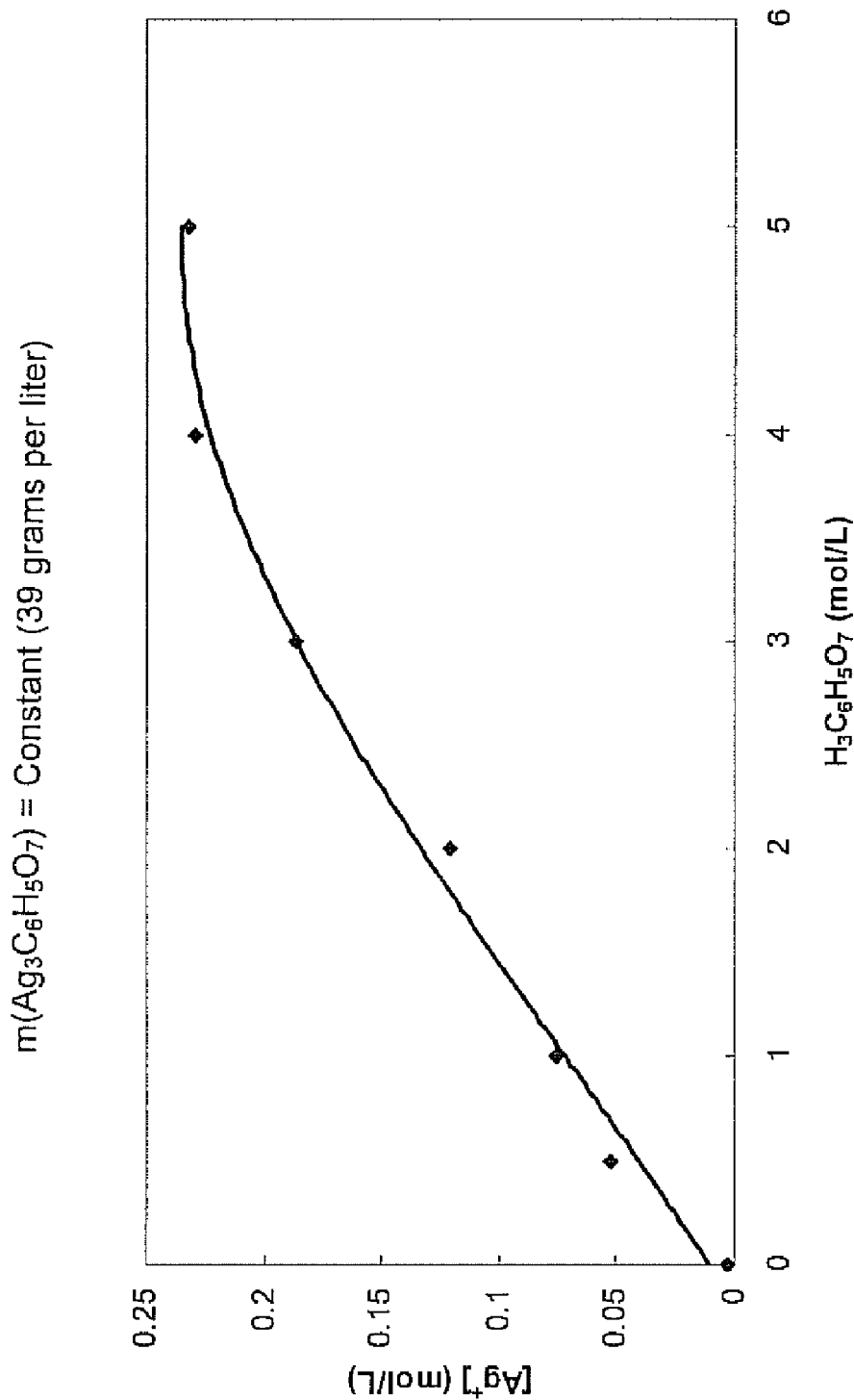
FIG. 2 is a graph depicting a "best fit" of silver ion concentration (in moles per liter) in an aqueous solution as a function of citric acid concentration (in moles per liter) in the aqueous solution, in which a substantially linear relationship is observed for a citric acid concentration between 0 moles per liter and about 4 moles per liter, in which about 39 grams per liter of solid trisilver citrate have been provided in the aqueous solution, and in which the maximum citric acid concentration is about 5 moles per liter.

FIG. 2 is a graph depicting a "best fit" of silver ion concentration (in moles per liter) in an aqueous solution/slurry containing citric acid and trisilver citrate under normal physico-chemical conditions, as a function of citric acid concentration (in moles per liter), wherein the initial concentration of trisilver citrate in the solution/slurry is 39 grams per liter (i.e., about 24.6 grams of silver per liter).

As can be seen again from FIG. 2, an increase in the citric acid concentration leads to an increase in the solubility of silver citrate and thus an increase in the silver ion concentration in the solution.

From FIG. 2, it can also be seen again that the relationship between citric acid concentration and silver ion concentration is substantially linear for citric acid concentrations between 0 moles per liter and about 4 moles per liter (i.e., about 800 grams per liter or about 45% by weight). At a citric acid concentration of about 4 moles per liter, the silver ion concentration is about 0.23 moles per liter (i.e., about 25 grams per liter or about 25000 ppm), which is equivalent to the concentration of silver provided by the trisilver citrate initially contained in the solution/slurry.

Figure 3:
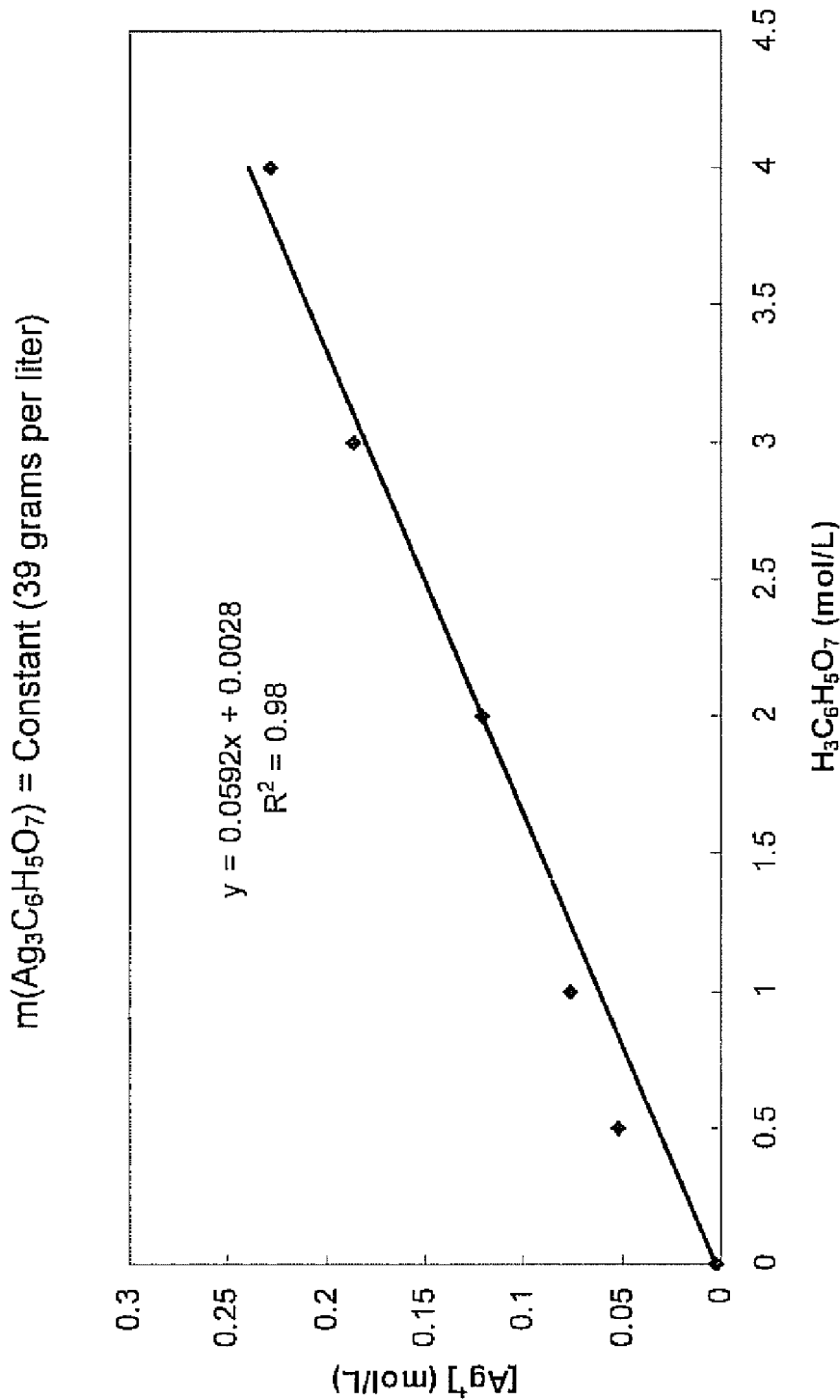
FIG. 3 is a graph depicting a "best fit" of silver ion concentration (in moles per liter) in an aqueous solution as a function of citric acid concentration (in moles per liter) in the aqueous solution, in which a substantially linear relationship is observed for a citric acid concentration between 0 moles per liter and 4 moles per liter, in which about 39 grams per liter of solid trisilver citrate have been provided in the aqueous solution, and in which the maximum citric acid concentration is about 4 moles per liter.

FIG. 3 is a graph depicting a "best fit" of silver ion concentration (in moles per liter) in an aqueous solution/slurry containing citric acid and trisilver citrate under normal physico-chemical conditions, as a function of citric acid concentration (in moles per liter), wherein the initial concentration of trisilver citrate in the solution/slurry is 39 grams per liter (i.e., about 24.6 grams per liter of silver).

As can be seen again from FIG. 3, an increase in the citric acid concentration leads to an increase in the solubility of silver citrate and thus an increase in the silver ion concentration in the solution.

From FIG. 3, it can also be seen again that the relationship between citric acid concentration and silver ion concentration is substantially linear for citric acid concentrations between 0 moles per liter and about 4 moles per liter (i.e., about 800 grams per liter or about 45% by weight). The linear relationship may be expressed by the following Equation:

$$y = 0.0592x + 0.0028 \tag{18}$$

where: y: is silver ion concentration in moles per liter
x: is citric acid concentration in moles per liter As can be seen, the slope of Equation 18 representing the linear relationship is 0.0592, which means that 0.0592 moles of silver ions are soluble in a liter of water for each mole per liter of citric acid which is present in the solution/slurry.

As a result, a silver ion concentration of about 0.12 moles per liter (i.e., about 13 grams per liter or about 13000 ppm) would appear to be achievable in a solution having a citric acid concentration of about 2 moles per liter (i.e., about 400 grams per liter or about 29% by weight), and a silver ion concentration of about 0.24 moles per liter (i.e. about 25 grams per liter or about 25000 ppm) would appear to be achievable in a solution having a citric acid concentration of about 4 moles per liter (i.e., about 800 grams per liter or about 45% by weight).

Figure 4:
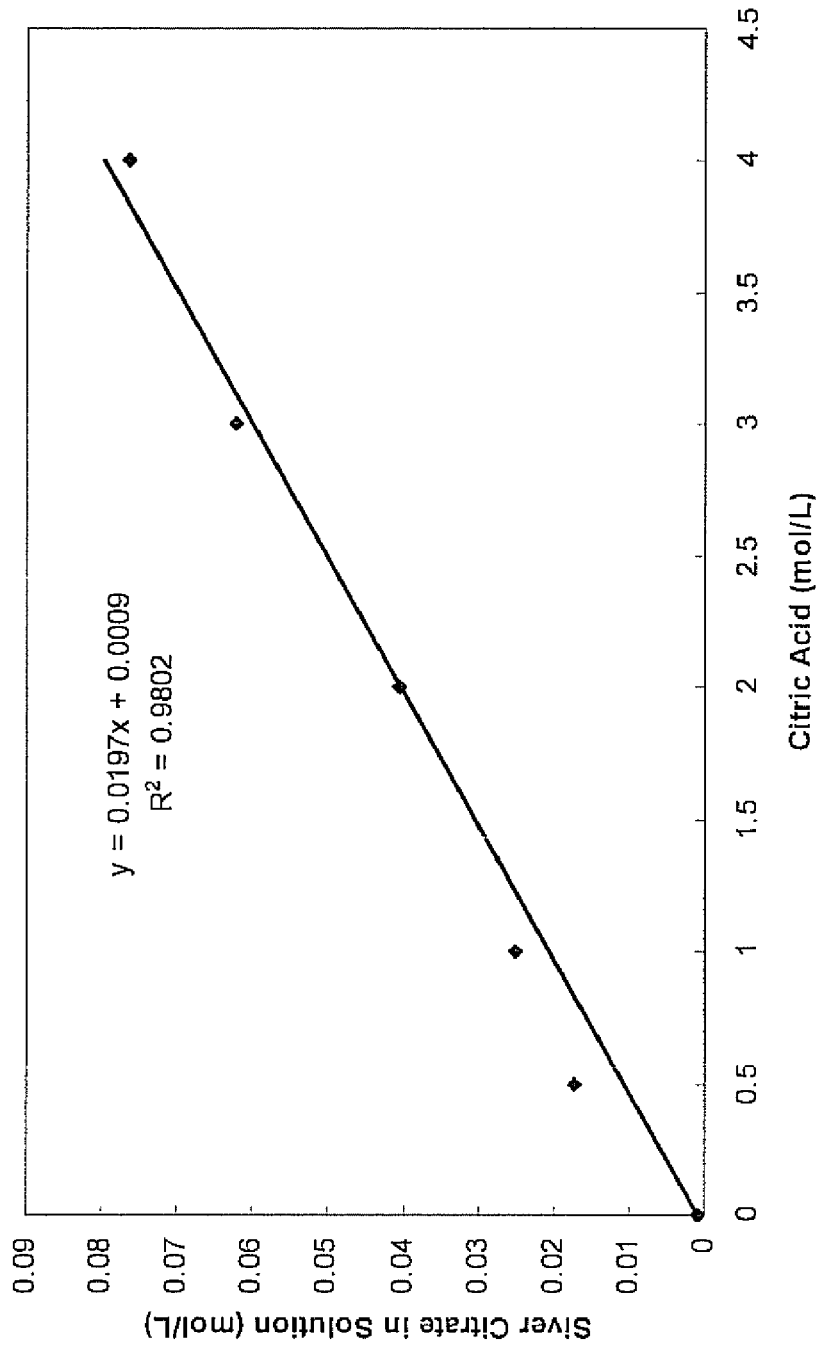
FIG. 4 is a graph depicting a "best fit" of dissolved trisilver citrate or trisilver citrate in solution (in moles per liter) in an aqueous solution as a function of citric acid concentration (in moles per liter) in the aqueous solution, in which the silver citrate concentration is about in which a substantially linear relationship is observed for a citric acid concentration between 0 moles per liter and 4 moles per liter, in which about 39 grams per liter of solid trisilver citrate have been provided in the aqueous solution, and in which the maximum citric acid concentration is about 4 moles per liter.

FIG. 4 is a graph depicting a "best fit" of dissolved trisilver citrate or trisilver citrate in solution (in moles per liter) in an aqueous solution/slurry containing citric acid and trisilver citrate under normal physico-chemical conditions, as a function of citric acid concentration (in moles per liter), wherein the initial concentration of trisilver citrate in the solution/slurry is 39 grams per liter (i.e., about 24.6 grams per liter of silver).

As can be seen again from FIG. 4, an increase in the citric acid concentration leads to an increase in the solubility of silver citrate and thus an increase in the dissolved trisilver citrate contained in the solution.

From FIG. 4, it can also be seen again that the relationship between citric acid concentration and dissolved trisilver citrate concentration is substantially linear for citric acid concentrations between 0 moles per liter and about 4 moles per liter (i.e., about 800 grams per liter or about 45% by weight). The linear relationship may be expressed by the following Equation:

$$y = 0.0197x + 0.0009 \tag{19}$$

where: y: is dissolved trisilver citrate concentration in moles per liter
x: is citric acid concentration in moles per liter As can be seen, the slope of Equation 19 representing the linear relationship is 0.0197, which means that 0.0197 moles of trisilver citrate are soluble in a liter of water for each mole per liter of citric acid which is present in the solution/slurry. It is noted that 0.0197 moles of trisilver citrate contains about 0.0124 moles of silver, based upon a molar weight of 513 grams per mole for trisilver citrate and a molar weight of 108 grams per mole for silver.

As a result, a silver ion concentration of about 0.12 moles per liter (i.e., about 13 grams per liter or about 13000 ppm) would appear to be achievable in a solution having a citric acid concentration of about 2 moles per liter (i.e., about 400 grams per liter or about 29% by weight), and a silver ion concentration of about 0.24 moles per liter (i.e. about 25 grams per liter or about 25000 ppm) would appear to be achievable in a solution having a citric acid concentration of about 4 moles per liter (i.e., about 800 grams per liter or about 45% by weight).

The maximum solubility of citric acid in water under normal physico-chemical conditions is theoretically about 1550 grams per liter (i.e., about 8 moles per liter or about 61% by weight). However, citric acid concentrations above about 4 moles per liter have been found to be practically difficult to achieve. It has been observed during laboratory experiments that an increase in citric acid concentration above about 4 moles per liter (i.e., about 800 grams per liter or about 45% by weight) appears to result in the formation of saturated solutions of citric acid and in the production of citric acid crystals.

It has been empirically observed that heating of solutions/slurries containing more than about 4 moles per liter of citric acid assists in dissolving the citric acid crystals, but subsequent cooling of the solutions/slurries results in further crystallization, suggesting that the practical saturation limit for citric acid under normal physico-chemical conditions is about 4 moles per liter (i.e., about 800 grams per liter or about 45% by weight).

As noted above, silver ion concentrations of about 25 grams per liter (i.e., about 25000 ppm or about 0.23 moles per liter) would appear to be achievable at citric acid concentrations above about 4 moles per liter (i.e., about 800 grams per liter or about 45% by weight).

As a result, based upon FIGS. 1-4 and upon observations made during laboratory experiments, it would appear that the present invention is capable of achieving concentrated solutions having a silver ion concentration of up to about 25 grams per liter (i.e., about 25000 ppm or about 0.23 moles per liter) in aqueous solutions of citric acid having a citric acid or citrate ion concentration of about 4 moles per liter (i.e., about 800 grams per liter or about 45% by weight) or higher.

Based upon FIGS. 1-4, it also appears that the silver ion concentrations which are achievable in aqueous solutions of citric acid having a citric acid or citrate ion concentration of between 0 moles per liter and about 4 moles per liter varies in a substantially linear relationship with the citric acid or citrate ion concentration, which linear relationship may be expressed as follows:

1. the ratio of citric acid or citrate ion concentration (in moles per liter) to silver ion concentration (in grams per liter) is at least about 0.16:1;
2. the ratio of citric acid or citrate ion concentration (in moles per liter) to silver ion concentration (in moles per liter) is at least about 17:1;
3. the ratio of citric acid or citrate ion concentration (in grams per liter) to silver ion concentration (in grams per liter) is at least about 30:1;
4. the ratio of citric acid or citrate ion concentration (in moles per liter) to trisilver citrate dissolvable in solution (in grams per liter) is at least about 0.099:1;
5. the ratio of citric acid or citrate ion concentration (in moles per liter) to trisilver citrate dissolvable in solution (in moles per liter) is at least about 51:1; and
6. the ratio of citric acid or citrate ion concentration (in grams per liter) to trisilver citrate dissolvable in solution (in grams per liter) is at least about 19:1.

Figure 5:
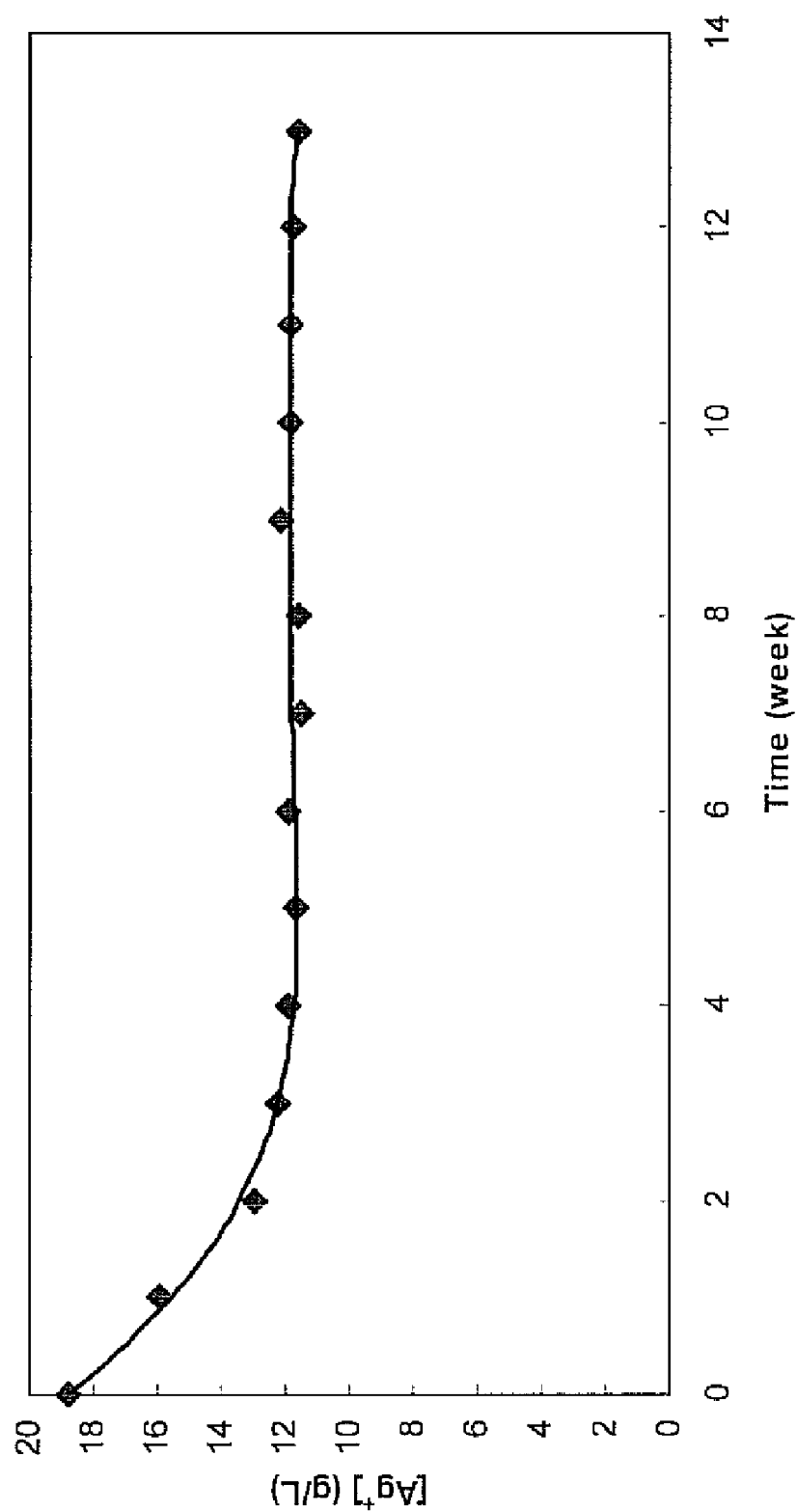
FIG. 5 is a graph depicting a "best fit" of silver ion concentration (in grams per liter) as a function of time in an aqueous solution prepared in accordance with the invention, in which the initial silver ion concentration is about 19 grams per liter.
Figure 6:
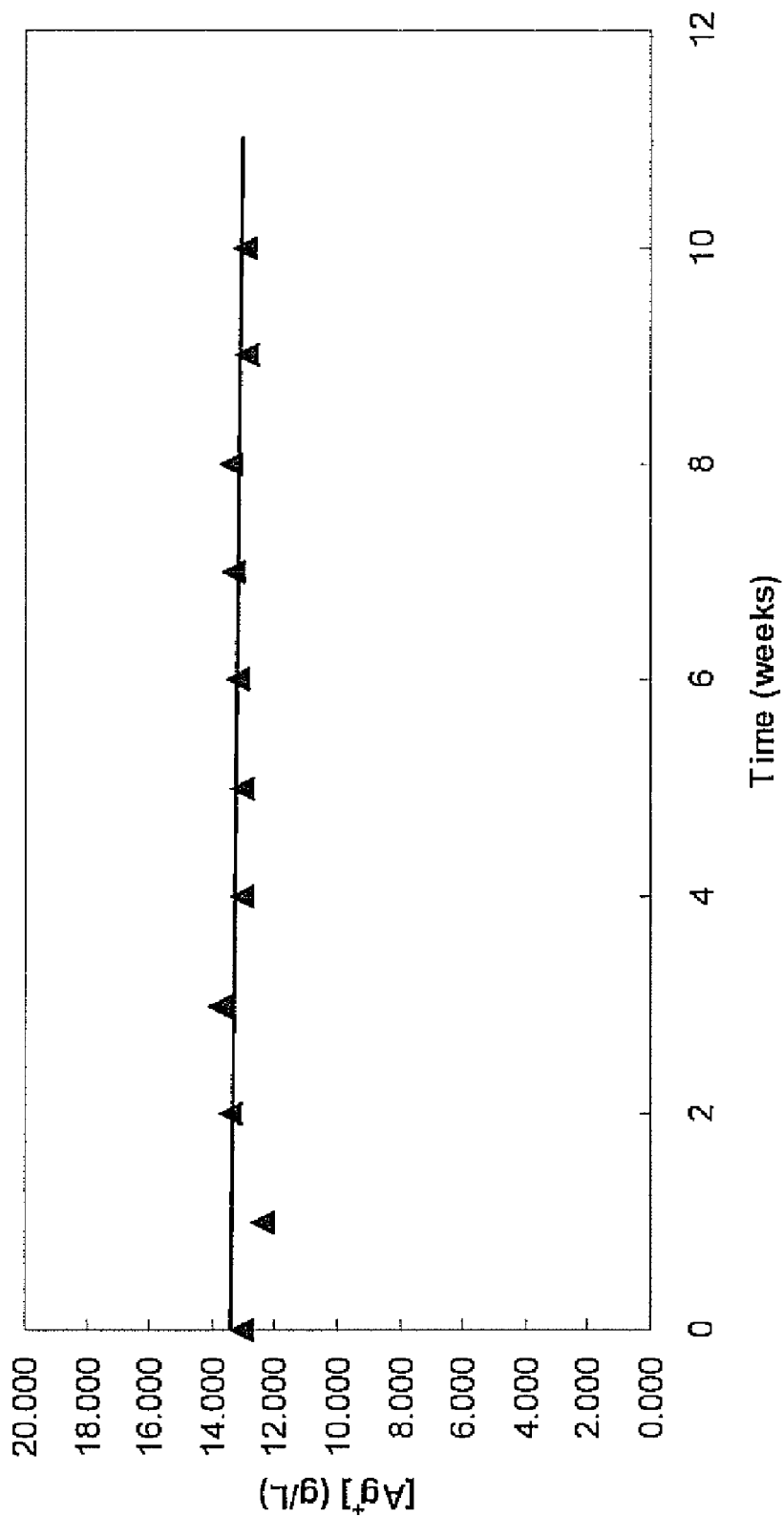
FIG. 6 is a graph depicting a "best fit" of silver ion concentration (in grams per liter) as a function of time in an aqueous solution prepared in accordance with the invention, in which the initial silver ion concentration is about 13 grams per liter.

FIG. 5 and FIG. 6 are graphs depicting a "best fit" of silver ion concentration as a function of time where the initial silver ion concentration is 19 grams per liter and 13 grams per liter respectively. FIG. 5 and FIG. 6 demonstrate the relative stability of concentrated solutions and/or diluted solutions prepared in accordance with the invention.

Referring to FIG. 5, the silver ion concentration of a concentrated solution prepared in accordance with the invention over a period of about 13 weeks (i.e., about 3 months) is depicted for a concentrated solution having an initial silver ion concentration of about 19 grams per liter (i.e., about 19000 ppm or about 0.18 moles per liter).

As depicted in FIG. 5, the silver ion concentration decreased over the three month period from about 19 grams per liter to about 12 grams per liter (i.e., about 12000 ppm or about 0.11 moles per liter).

Referring to FIG. 6, the silver ion concentration of a concentrated solution prepared in accordance with the invention over a period of about 10 weeks (i.e. about 2-3 months) is depicted for a concentrated solution having an initial silver ion concentration of about 13 grams per liter (i.e., about 13000 ppm or about 0.12 moles per liter).

As depicted in FIG. 6, the silver ion concentration did not change significantly over the 2-3 month period from the initial silver ion concentration of about 13 grams per liter.

In general, it has been found that concentrated solutions prepared in accordance with the invention which have a silver ion concentration which is less than or equal to about 13 grams per liter (i.e., about 13000 ppm or about 0.12 moles per liter) are relatively stable under normal physico-chemical conditions. In addition, it has been found that diluted solutions which have a silver ion concentration which is less than or equal to about 13 grams per liter and which have been prepared from concentrated solutions having a silver ion concentration which is greater than about 13 grams per liter are also relatively stable, provided that the appropriate ratio of citric acid or citrate ion concentration to silver ion concentration is maintained in the diluted solutions.

Concentrated solutions and diluted solutions having a silver ion concentration which is between about 13 grams per liter (i.e., about 13000 ppm or about 0.12 moles per liter) and about 15 grams per liter (i.e., about 15000 ppm or about 0.14 moles per liter) have generally been found to be reasonably stable, but not as reliably stable as concentrated solutions and diluted solutions having a silver ion concentration which is less than or equal to about 13 grams per liter.

The stability of concentrated solutions and diluted solutions may be enhanced by adding a stabilizing agent to the solutions. It has been found that glycerol may be a suitable stabilizing agent for use in the invention.

Concentrated solutions and diluted solutions prepared in accordance with the invention may be used for a range of antimicrobial and disinfectant applications. By way of non-limiting examples, concentrated solutions and diluted solutions prepared in accordance with the invention may be useful for various specific applications such as prevention of biofilm formation, disinfection of swimming pools, hot tubs, spas, disinfection of surgical instruments, hospitals, public buildings, aircrafts, in topical wound dressings (e.g. bandages), as additives for cleaning agents and in any other applications where the suppression of micro-organisms may be required.

Another potential advantage of concentrated solutions and diluted solutions prepared in accordance with the invention is that both silver ions and citrate ions are known for their antimicrobial properties. As a result, the combination of silver ions and relatively high concentrations of citrate ions in the concentrated solutions and the diluted solutions prepared in accordance with the invention may provide superior antimicrobial properties in comparison with compositions containing only silver ions or only citrate ions.

Although the invention has been described primarily in the context of concentrated solutions and diluted solutions prepared from trisilver citrate and citric acid as starting materials, it should be noted that similar solutions can be prepared when other carboxylic or hydroxy-carboxylic acids are used in place of citric acid, such as glycolic acid, lactic acid, α-hydroxybutyric acid, mandelic acid, glyceric acid, malic acid, tartaric acid, meso-tartaric acid or the like, in combination with silver salts of such acids.

The following experimental Examples illustrate features and aspects of the invention.

EXAMPLE 1

7.6849 grams of silver nitrate ($AgNO_3$) (i.e., containing about 4.88 grams of silver ions) were dissolved in 100 mL of reverse osmosis (RO) purified water. To this solution 10 mL of 28% by volume sodium hydroxide (NaOH) solution was added. After precipitation of a dark brown silver oxide ($Ag_2O$) precipitate occurred, the slurry was mixed for another 20 minutes. The slurry was left to allow the brown silver oxide precipitate to settle and a clear colorless solution was then decanted. The brown silver oxide precipitate was then carefully rinsed with reverse osmosis water until the pH of the washing solution was about 7. After the washing step, a solution of 155 grams of solid citric acid ($H_3C_6H_5O_7$) dissolved in 100 mL of reverse osmosis (RO) purified water (i.e., about 1550 grams per liter, about 8 moles per liter, or about 61% by weight) was added to the wet brown silver oxide precipitate. Upon the addition of the highly concentrated citric acid solution the color of the precipitate changed from dark brown to white. This change in appearance indicated a transformation of the brown silver oxide precipitate to white trisilver citrate ($Ag_3C_6H_5O_7$) precipitate. With heating the white trisilver citrate precipitate disappeared and a clear, dense, colorless solution was obtained. The solution was boiled down to 250 mL to provide a concentrated solution which contained about 620 grams per liter of citric acid (i.e. about 3 moles per liter or about 38% by weight).

The chemical analysis of the concentrated solution showed that the silver ion concentration was about 18.8 grams per liter (i.e., a total of about 4.7 grams of silver ions in the concentrated solution) indicating that only about 3.7% of the silver ions contained in the silver nitrate were lost during the preparation of the concentrated solution. The density of the concentrated solution was about 1.26 g/cm$^3$ and the final product solution had a pH of 1.

The appearance of the clear colorless concentrated solution did not change for over three months. However some crystallization at the bottom of the container occurred during the three months. It appeared that the crystals were first colorless, then white and finally grayish. Chemical analysis of the concentrated solution determined that the silver ion concentration in the concentrated solution gradually decreased over time. Specifically, the silver ion concentration in the concentrated solution was reduced over time from an initial silver ion concentration of 18.8 grams per liter to a final silver ion concentration of about 11 grams per liter after 3 months.

EXAMPLE 2

Starting with 7.8651 grams of silver nitrate ($AgNO_3$) (i.e., containing about 4.99 grams of silver ions), an aqueous clear colorless solution containing only silver ions and citrate ions was obtained in the manner as described in Example 1. 35 mL of glycerol ($C_3H_5(OH)_3$) were added to this solution and the solution was diluted exactly to 250 mL to provide a concentrated solution which contained about 620 grams per liter of citric acid (i.e., about 3 moles per liter or about 38% by weight).

Chemical analysis of the concentrated solution found that the silver ion concentration was 18.96 grams per liter (i.e., a total of about 4.74 grams of silver ions in the concentrated solution), showing that about 5.1% of the silver ions contained in the silver nitrate were lost during the process.

Furthermore, the concentrated solution was relatively stable over a period of three months. Some formation of crystals at the bottom of the container was observed. Importantly, the silver ion concentration in the concentrated solution decreased, but to a significantly lesser extent than was observed in Example 1. Specifically, over a period of 3 months the silver ion concentration in the concentrated solution decreased from 18.96 grams per liter to about 17 grams per liter, indicating that the use of glycerol as a stabilizing agent can significantly enhance the stability of solutions prepared in accordance with the invention.

EXAMPLE 3

7.8614 grams of silver nitrate ($AgNO_3$) (i.e., containing about 4.99 grams of silver ions) were dissolved in 100 mL of reverse osmosis (RO) purified water. To this solution 7 mL of 28% by volume ammonium hydroxide ($NH_4OH$) solution was added to obtain a clear colorless solution containing silver diamino complex $[Ag(NH_3)_2]^+$. When a clear colorless solution was obtained, a solution of 155 grams of solid citric acid ($H_3C_6H_5O_7$) dissolved in 100 mL of reverse osmosis (RO) purified water (i.e., about 1550 grams per liter, about 8 moles per liter, or about 61% by weight) was added to the silver diamino complex solution at room temperature. Initially, a formation of white silver citrate ($Ag_3C_6H_5O_7$) precipitate was observed, which dissolved upon heating of the solution to about 50° C.-60° C. While the solution was being heated, 35 mL of glycerol as a stabilizing agent was mixed with the solution and the temperature of 50° C.-60° C. was maintained for the next 10 minutes. The solution was then boiled to a volume of about 200 mL to 220 mL. The boiled solution was then diluted with reverse osmosis (RO) purified water to a final volume of 250 mL to provide a concentrated solution which contained about 620 grams per liter of citric acid (i.e., about 3 moles per liter or about 38% by weight).

The clear and colorless concentrated solution had a pH of about 1, a density of approximately 1.3 g/cm$^3$, and a silver ion concentration of 19.51 grams per liter (i.e., a total of about 4.88 grams of silver ions), which was slightly below the expected silver ion concentration (19.97 grams per liter or 4.99 grams), based on the initial amount of silver nitrate.

With aging the concentrated solution exhibited a gradual decrease in silver ion concentration from 19.51 grams per liter to about 13 grams per liter during a period of three months. Further aging of the concentrated solution did not lead to a significant decrease in the silver ion concentration.

It is noted that in this Example 3, a "counter-ion" ($NH_4^+$) was present in the concentrated solution. As a result, Example 3 demonstrates that a presence of a so-called "counter-ion" in solutions prepared in accordance with the invention, even with the addition of glycerol as a stabilizing agent, may result in a significant decrease in the silver ion concentration in the concentrated solution and a reduction in the stability of the concentrated solution.

EXAMPLE 4

7.8624 grams of silver nitrate ($AgNO_3$) (i.e., containing about 4.99 grams of silver ions) were dissolved in 150 mL of reverse osmosis (RO) purified water. In a separate beaker 4 grams of sodium citrate ($Na_3C_6H_5O_7$) was dissolved in 50 mL of reverse osmosis (RO) purified water. While stirring the silver nitrate solution with a magnetic stirrer, the sodium citrate solution was added to the silver nitrate solution and the formation of white trisilver citrate ($Ag_3C_6H_5O_7$) precipitate was observed.

After mixing for 20 minutes, the resulting combined solution were left to settle. The white trisilver citrate precipitate was separated from the combined solution by filtration and the silver ion concentration in the combined solution as found by chemical analysis to be about 2.15 grams per liter.

The white trisilver citrate precipitate was carefully rinsed with reverse osmosis (RO) purified water. A solution of 155 grams of solid citric acid ($H_3C_6H_5O_7$) dissolved in 100 mL of reverse osmosis (RO) purified water was added to the trisilver citrate ($Ag_3C_6H_5O_7$) precipitate. With mild heating the white trisilver citrate precipitate dissolved and a clear colorless solution was obtained. The volume of the solution was then adjusted to about 250 mL to provide a concentrated solution which contained about 620 grams per liter of citric acid (i.e., about 3 moles per liter or about 38% by weight).

The silver ion concentration in the concentrated solution was about 20.31 grams per liter. Having regard to the amount of silver ions provided by the silver nitrate (i.e., about 4.99 grams), the silver ion concentration measured in the concentrated solution suggests that that volume of the concentrated solution was actually less than 250 mL, with the result that the citric acid concentration in the concentrated solution was actually greater than 3 moles per liter or 38% by weight. The concentrated solution was stored in a clear bottle. No change in color was observed over a period of four months, but the silver ion concentration in the concentrated solution decreased during the four month period from about 20 grams per liter to about 14 grams per liter.

EXAMPLE 5

A concentrated solution having a silver ion concentration of about 20 grams per liter and a citric acid concentration of about 620 grams per liter (i.e., about 3 moles per liter or about 38% by weight) was prepared exactly as described in Example 4 above.

The concentrated solution was diluted with reverse osmosis (RO) purified water to obtain a series of diluted solutions having silver ion concentrations ranging from 9 grams per liter to 20 grams per liter.

It was observed that the diluted solutions having a silver ion concentration less than 13 grams per liter (i.e., 13000 ppm or about 0.12 moles per liter) were relatively stable and did not show a significant decrease in silver ion concentration as long as the citric acid concentration was sufficient to maintain the trisilver citrate in the diluted solutions and thus prevent precipitation of the trisilver citrate. As previously described, for a silver ion concentration of 13 grams per liter (i.e., 13000 ppm or about 0.12 moles per liter), the required citric acid concentration to prevent the precipitation of the trisilver citrate is at least about 400 grams per liter (i.e., about 2 moles per liter or about 29% by weight).

In this document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The embodiments of the invention in which an exclusive property or privilege is claimed are defined as follows:

1. A concentrated solution comprising water, hydrogen ions, citrate ions and silver citrate complexes consisting essentially of silver ions and citrate ions, wherein the silver ions have a concentrated silver ion concentration in the concentrated solution, wherein the citrate ions have a concentrated citrate ion concentration in the concentrated solution, wherein the concentrated citrate ion concentration is at least 30 times the concentrated silver ion concentration by weight, wherein the concentrated citrate ion concentration is at least 300 grams per liter, and wherein the concentrated silver ion concentration is greater than 10 grams per liter.

2. The concentrated solution as claimed in claim 1 wherein the concentrated citrate ion concentration is between 300 grams per liter and 1550 grams per liter and wherein the concentrated silver ion concentration is between greater than 10 grams per liter and 25 grams per liter.

3. The concentrated solution as claimed in claim 1 wherein the concentrated citrate ion concentration is between 300 grams per liter and 800 grams per liter and wherein the concentrated silver ion concentration is between greater than 10 grams per liter and 25 grams per liter.

4. The concentrated solution as claimed in claim 1 wherein the concentrated silver ion concentration is greater than 13 grams per liter.

5. The concentrated solution as claimed in claim 1 wherein the concentrated solution consists essentially of the water, the hydrogen ions, the citrate ions and the silver citrate complexes.

6. The concentrated solution as claimed in claim 4, further comprising an amount of a stabilizing agent.

7. The concentrated solution as claimed in claim 6 wherein the stabilizing agent is comprised of glycerol.

8. The concentrated solution as claimed in claim 6 wherein the concentrated solution consists essentially of the water, the hydrogen ions, the citrate ions, the silver citrate complexes and the stabilizing agent.

9. A diluted solution prepared by adding water to a concentrated solution comprising water, hydrogen ions, citrate ions and silver citrate complexes consisting essentially of silver ions and citrate ions, wherein the silver ions have a concentrated silver ion concentration in the concentrated solution, wherein the silver ions have a diluted silver ion concentration in the diluted solution, wherein the citrate ions have a concentrated citrate ion concentration in the concentrated solution, wherein the citrate ions have a diluted citrate ion concentration ion the diluted solution, wherein the concentrated citrate ion concentration is at least. 30 times the concentrated silver ion concentration by weight, wherein the diluted citrate ion concentration is at least 30 times the diluted silver ion concentration by weight, and wherein the concentrated silver ion concentration is greater than 10 grams per liter.

10. The diluted solution as claimed in claim 9 wherein the concentrated silver ion concentration is greater than 13 grams per liter and wherein the diluted silver ion concentration is less than or equal to 13 grams per liter.

11. The diluted solution as claimed in claim 9 wherein the diluted solution consists essentially of the water, the hydrogen ions, the citrate ions and the silver citrate complexes.

12. A method for preparing a concentrated solution comprising water, hydrogen ions, citrate ions and silver citrate complexes consisting essentially of silver ions and citrate ions, the method comprising:
  (a) providing an amount of trisilver citrate;
  (b) providing an amount of citric acid, wherein the amount of citric acid is at least 19 times the amount of the trisilver citrate by weight; and
  (c) mixing the trisilver citrate and the citric acid in an amount of water to produce the concentrated solution, Wherein the amount of the water is selected so that the citrate ions have a concentrated citrate ion concentration in the concentrated solution Which is at least 300 grams per liter, and wherein the amount of trisilver citrate is selected so that the silver ions have a concentrated silver ion concentration in the concentrated solution which is greater than 10 grams per liter.

13. The method as claimed in claim 12 wherein the concentrated solution has a concentrated silver ion concentration in the concentrated solution which is between greater than 10 grams per liter and 25 grains per liter.

14. The method as claimed in claim 12 wherein the concentrated solution has a concentrated silver ion concentration in the concentrated solution which is greater than 13 grams per liter.

15. The method as claimed in claim 12 wherein the concentrated solution has a concentrated silver ion concentration in the concentrated solution which is between greater than 10 grams per liter and 13 grams per liter.

16. The method as claimed in claim 12 wherein the concentrated solution consists essentially of the water, the hydrogen ions, the citrate ions and the silver citrate complexes.

17. The method as claimed in claim 14, further comprising adding an amount of a stabilizing agent to the concentrated solution.

18. The method as claimed, in claim 17 wherein the stabilizing agent is comprised of glycerol.

19. The method as claimed in claim 17 wherein the concentrated solution consists essentially of the water, the hydrogen ions, the citrate ions, the silver citrate complexes and the stabilizing agent.

20. The method as claimed in claim 12, further comprising adding water to the concentrated solution to prepare a diluted solution, wherein the silver ions have a diluted silver ion concentration in the diluted solution which is less than the concentrated silver ion concentration, wherein the citrate ions have a diluted citrate ion concentration in the diluted solution, and wherein the diluted citrate ion concentration is at least 30 times the diluted silver ion concentration by weight.

21. The method as claimed in claim 20 wherein the diluted solution consists essentially of the water, the hydrogen ions, the citrate ions and the silver citrate complexes.

22. The method as claimed in claim 14, further comprising adding water to the concentrated solution to prepare a diluted solution, wherein the silver ions have a diluted silver ion concentration in the diluted solution, wherein the citrate ions have a diluted citrate ion concentration in the diluted solution, wherein the diluted silver ion concentration is less than or equal to 13 grams per liter, and wherein the diluted citrate ion concentration is at least 30 times the diluted silver ion concentration by weight.

23. The method as claimed in claim 22 wherein the diluted solution consists essentially of the water, the hydrogen ions, the citrate ions and the silver citrate complexes.

24. The diluted solution as claimed in claim 9 wherein the concentrated silver ion concentration is greater than 15 grams per liter and wherein the diluted silver ion concentration is less than or equal to 15 grams per liter.

25. The method as claimed in claim 12 wherein the concentrated solution has a concentrated silver ion concentration in the concentrated solution which is greater than 15 grams per liter.

26. The method as claimed in claim 25, further comprising adding water to the concentrated solution to prepare a diluted solution, wherein the silver ions have a diluted silver ion concentration in the diluted solution, wherein the citrate ions have a diluted citrate ion concentration in the diluted solution, wherein the diluted silver ion concentration is less than or equal to 15 grams per liter, and wherein the diluted citrate ion concentration is at least 30 times the diluted silver ion concentration by weight.

27. The method as claimed in claim 26 wherein the diluted solution consists essentially of the water, the hydrogen ions, the citrate ions and the silver citrate complexes.

* * * * *

UNITED STATES PATENT AND TRADEMARK OFFICE
CERTIFICATE OF CORRECTION

PATENT NO. : 8,399,028 B2
APPLICATION NO. : 12/191477
DATED : March 19, 2013
INVENTOR(S) : Stojan Djokic Page 1 of 1

It is certified that error appears in the above-identified patent and that said Letters Patent is hereby corrected as shown below:

In the Specifications:

Column 9
Line 25, change "$[Ag_3(C_6H_5O_7)_{n+1}]^{3n-}3nH+$" to --$[Ag_3(C_6H_5O_7)_{n+1}]^{3n-} + 3nH^+$--

Column 11
Line 67, change "$[Ag_3(C_6H_5O_7)_{n+1}]^{3-}$" to --$[Ag_3(C_6H_5O_7)_{n+1}]^{3n-}$--

In the Claims:

Column 20
Line 22 (Claim 9, line 9), change "ion the" to --in the--.
Line 46 (Claim 12, line 11), change "Wherein" to --wherein--.
Line 48 (Claim 12, line 13), change "Which" to --which--.

Signed and Sealed this
Ninth Day of July, 2013

Teresa Stanek Rea
*Acting Director of the United States Patent and Trademark Office*